United States Patent [19]

Szebenyi et al.

[11] Patent Number: 4,888,172

[45] Date of Patent: Dec. 19, 1989

[54] PHARMACEUTICAL FOR TREATING TUMORS AND METHODS FOR MAKING IT

[75] Inventors: Emil Szebenyi, Little Falls; Shogen Kuslima, Somerset, both of N.J.

[73] Assignee: Alfaceu Corporation, Bloomfield, N.J.

[21] Appl. No.: 776,798

[22] Filed: Sep. 17, 1985

Related U.S. Application Data

[63] Continuation-in-part of Ser. No. 643,808, Aug. 23, 1984, abandoned, which is a continuation of Ser. No. 422,034, Sep. 23, 1982, abandoned.

[51] Int. Cl.$^4$ ............................................. A61K 35/54
[52] U.S. Cl. ..................................... 424/105; 424/95; 514/2

[58] Field of Search .................................. 424/95, 105

[56] References Cited

PUBLICATIONS

Chem. Abst. Sabj. Index (General) 10th Collect. vol. 86-95, (1977-1981) p. 7868GS.

Primary Examiner—Sam Rosen
Attorney, Agent, or Firm—Mark H. Jay

[57] ABSTRACT

*Rana pipiens* embryos are grown to a predetermined stage of development. The embryos are then subjected to mechanical processing to produce an extract. The extract is freed of endotoxins, and diluted to a standard potency. The resulting pharmaceutical is administered intraveneously to necrotize tumors.

17 Claims, 2 Drawing Sheets

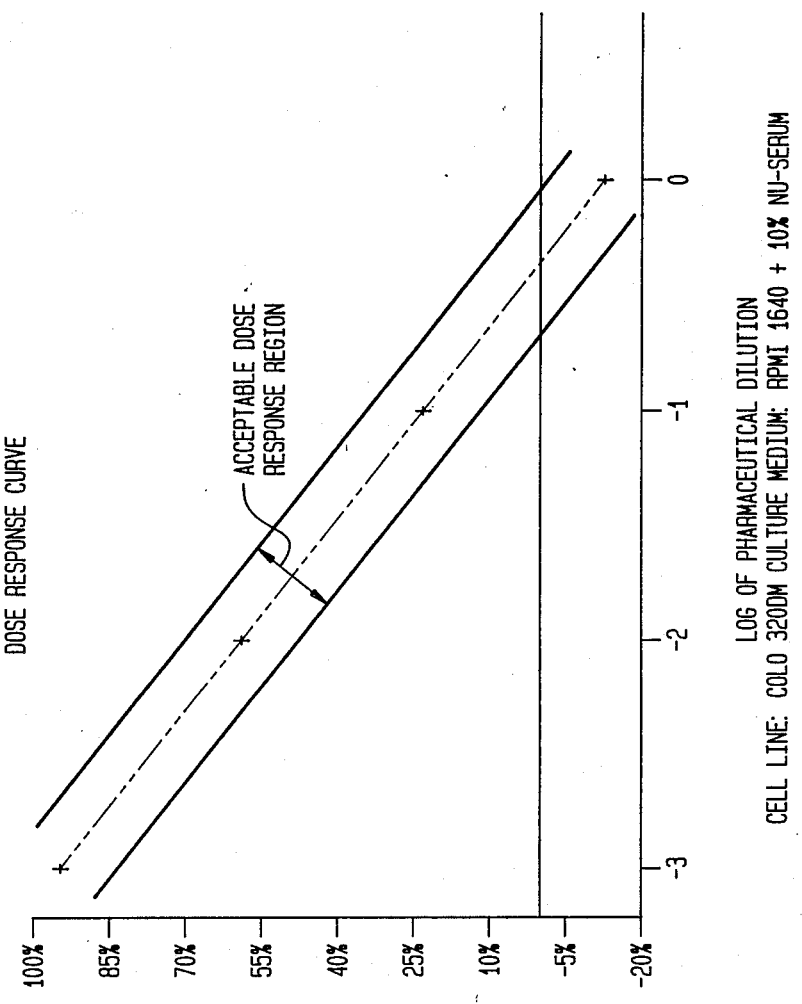

PHARMACEUTICAL FOR TREATING TUMORS AND METHODS FOR MAKING IT

CROSS-REFERENCE TO RELATED APPLICATION

This application is a continuation-in-part of a pending commonly-owned application filed Aug. 23, 1984, accorded Ser. No. 643,808, and entitled "Non-Specific Tumor Treatment" (now abandoned), which is a continuation application of Ser. No. 422,034, filed Sept. 23, 1982 (now abandoned).

BACKGROUND OF THE INVENTION

The invention relates to pharmaceuticals, and more particularly relates to pharmaceuticals for use in treating tumors in humans.

At present, tumors are treated either by chemotherapy, radiotherapy or surgery. Each of these therapies has disadvantages.

It would be advantageous to avoid the disadvantages of chemotherapy, radiotherapy and surgery.

One object of the invention is to provide a pharmaceutical therapy for tumors in humans.

An additional object is to provide a biologic therapy for tumors in humans.

Another object is to provide such a therapy which has less disadvantageous side effects than those of other known therapies.

A further object is to provide such a therapy for use with more than one type of tumor.

Yet another object is to provide such a therapy for use in a relatively high fraction of cases.

Still a further object is, in general, to improve on known therapies for treatment of tumors in humans.

In accordance with the invention, there is provided a pharmaceutical for treatment of tumors in humans. The pharmaceutical is derived from eggs of a vertebrate species; in a preferred embodiment, the pharmaceutical is derived from embryos of the *Rana pipiens* frog. The development of the embryos is advantageously halted before gastrulation and preferably at or before the full blastulae (128 cell) stage.

In further accordance with the invention, an extract is formed from the embryos and is detoxified. The final product may be a liquid or a lyophilized solid.

In accordance with the invention, the pharmaceutical is administered to a patient in a therapeutically effective quantity. The preferred method of administration is intravenous injection, but intratumor injection can be used instead.

In the preferred embodiment, the rate of tumor necrosis is limited; there is a limit to the body's ability to reabsorb necrotic cell material and excessive tumor necrosis can itself be an unhealthy condition. To do this, the patient's body functions are advantageously monitored during administration and administration is halted when body functions indicate an excessive rate of tumor necrosis. Such monitoring may advantageously be carried out by monitoring the patient's blood urea nitrogen (BUN), uric acid, total urea, or creatinine, and comparing the current levels of these substances with those existing at the start of treatment.

BRIEF DESCRIPTION OF THE DRAWINGS

The invention will be better understood with reference to the following illustrative and non-limiting drawings, in which:

FIG. 2 is a chart indicating acceptable potency in accordance with a preferred embodiment of the invention.

DETAILED DESCRIPTION OF PREFERRED EMBODIMENTS

Figure 1:
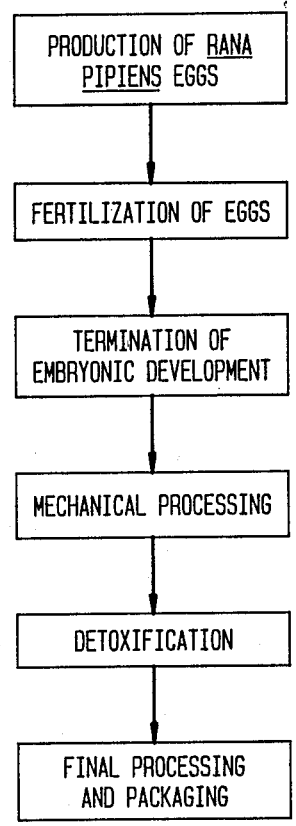
FIG. 1 is a flowchart of the process in accordance with a preferred embodiment of the invention.

In manufacturing pharmaceuticals, stringent care must be exercised to avoid contamination of the product made and infection of the persons involved. For example, appropriate vessels (such as Nalgene) must be used, appropriate sterilization steps (such as wearing of sterile garments, autoclaving, rinsing in pyrogen-free water, etc.) must be taken, appropriate transfer techniques (such as transfer under a laminar flow hood) must be employed, and so forth. Furthermore, appropriate quality control steps must be employed (e.g. intermediates must be examined for suitability for further processing and freedom from endotoxins must be verified as by a limulus amoebocyte test or rabbit pyrogen test) to verify that the end product satisfies all applicable requirements. While occasional reference is made below to steps and techniques of this nature, the failure to mention such steps and techniques is not an indication that they may be omitted.

A. Production of Vertebrate Embryos

In the preferred embodiment, *Rana pipiens* eggs are produced by induced ovulation (so that their development takes place in a highly controlled manner) and fertilized under controlled conditions outside the body of the female frog. During the breeding season, which begins in early May, induced ovulation cannot be used because *Rana pipiens* produces eggs in an uncontrollable manner.

Only large, healthy and vigorous gravid female *Rana pipiens* are selected for induced ovulation. They are separated from male *Rana pipiens* and are maintained at a temperature of 6° C. for a period of three days in tanks filled with one inch of tap water. This temperature is preferred, but other temperatures can be used if the other variables in the fertilization process are accordingly adjusted; the rate at which the eggs develop is dependent upon temperature. The waver level is chosen to keep the heads of the *Rana pipiens* above water at all times, because gravid *Rana pipiens* are lethargic and can drown if their heads are not kept above the water level.

For each selected female, a petri dish is preferably filled with 10 cubic centimeters of tested spring water. Tested spring water is fresh spring water which has been tested to support life of *Rana pipiens* and its embryos. Tested spring water produces the best results, but it is alternatively possible to use 0.9% saline solution instead.

Preferably, each selected female is induced to ovulate by introducing fresh *Rana pipiens* pituitary glands into her body, but a combination of dried pituitary matter and progesterone may be used instead. The glands are removed from other *Rana pipiens* (which may advantageously but not necessarily be killed by over-etherization) and placed in the appropriate liquid-containing petri dish prior to introduction. The number of glands used to induce ovulation varies with the month in which the ovulation is to be induced; the preferred number of glands is set forth in TABLE 1.

TABLE 1

| MONTH | # FEMALE PITUITARY GLANDS |
|---|---|
| September | 5 |
| October | 5 |
| November | 5 |
| December | 5 |
| January | 5 |
| February | 5 |
| March | 5 |
| April | Ovulation Spontaneous |
| May | BREEDING SEASON - NO INDUCED OVULATION |
| June | BREEDING SEASON - NO INDUCED OVULATION |
| July | BREEDING SEASON - NO INDUCED OVULATION |
| August | BREEDING SEASON - NO INDUCED OVULATION |

Note: Male pituitary glands may be substituted for female pituitary glands, but one female pituitary gland is equivalent to two male pituitary glands and the quantities used must be adjusted accordingly.

The appropriate number of glands is placed in the corresponding liquid-containing petri dish. Each selected female is brought to room temperature (22° C.). Dish by dish, the glands are drawn up into a syringe and introduced into the right lower quadrant of the abdoman of the corresponding selected female by injection through an 18 gauge needle.

The selected females are then replaced in tanks filled with one inch of spring or pond water. Flat rocks are placed in the bottom of each tank, so that the females can rest upon them and remain above the water line. The tanks are covered with warehouse cloth and advantageously kept at room temperature (22° C.) for 48 hours. The eggs produced by the gravid females are then, in accordance with the preferred embodiment, fertilized outside their bodies.

To do this, male *Rana pipiens* are sacrificed (as by over-etherization) and their testes are removed. Enough males must be killed to yield at least 4 testes per gravid female. (Advantageously, their pituitary glands are also removed for use in inducing ovulation in a subsequent batch of females.) The testes are cleaned of connective tissue and star-shaped fat.

For each gravid female, four petri dishes are filled with 10 cubic centimeters of tested pond or spring water. At least one pair of testes is placed in each dish, and the testes are macerated (as by chopping) to form a milky sperm suspension. The maceration must be conducted in such a manner as not to chop the sperm. The eggs are then removed from each gravid female by pressing her abdomen towards her posterior. The egg production of each female is distributed evenly among the four suspension-filled petri dishes, with no more than 300 eggs per dish.

The eggs are left in the suspension for about 3 to 4.5 hours at room temperature. During the first hour, the sperm suspension and eggs in the dish are intermittently swirled so that the eggs are always covered by the sperm suspension. After the 3 to 4.5 hours have passed, at least 10 and no more than 15 eggs from each dish are put into a well slide and examined. When 80% cleavage of the *Rana pipiens* embryos is observed, the corresponding dish is collected; the embryos are then in at least the 4 cell stage of development and must be at the full blastulae (128 cell) stage or earlier. After about three hours have passed, the embryos will be at the 4 to 8 cell stage of development.

If the embryos are at a comparatively early (4 to 8 cell) stage of development, they may be collected without any further processing. As the embryos reach later stages of development, tissue debris forms and must be removed before further processing takes place. It is now preferred to collect the embryos at the 4 to 8 cell stage of development, but this is because of convenience in processing and is not required.

All collected embryos may then be scraped into containers and stored in frozen form at or below −85° C. This storage is not essential for the practice of the invention; it is preferred only when it is convenient to carry out subsequent processing in batches.

B. Mechanical Processing of the Embryos

If the embryos to be processed have been frozen, they are thawed, as by a 37° C. water bath. The thawed or never-frozen embryos are then homogenized, preferably under a laminar flow hood to avoid contamination.

In the preferred embodiment, the homogenization is carried out by using a variable speed Brinkmann homogenizer at setting number 6 for about one minute and repeated as necessary until homogenization is complete, but this is not required and any sanitary method for accomplishing thorough homogenization can be used. Homogenization is complete when the suspension appears homogenous with no sign of intact eggs.

In the preferred embodiment, the homogenized embryos are centrifuged (at 4° C. to 8° C.) in two stages, with the second stage being repeated twice, to extract therefrom the maximum quantity of supernatant fluid. This is not required and other processing techniques (including, but not limited to pressing, filtration under pressure, etc.) can be used instead.

In the preferred embodiment, the homogenate is transferred into centrifuge bottles under sterile conditions, e.g. under laminar flow. In the preferred embodiment, the first centrifugation is conducted at 12,000 rpm for 16 hours (+/−3 hours) in an IEC Model B20A centrifuge, using 250 milliliter screw-top bottles (IEC bottle number 2050) in IEC rotor number 872. The supernatant fluid is decanted into a sterile vessel under appropriate conditions (as under laminar flow) and the sediment is subjected to further processing.

In the preferred embodiment, the sediment is transferred to ultracentrifuge bottles (such as Beckman 250 milliliter bottles number 334205) and centrifuged at 17,000 rpm for 16 hours (+/−3 hours) in a Beckman Model L8-70 ultracentrifuge, using a TI-19 rotor. The supernatant fluid is decanted as before, and the remaining sediment is recentrifuged under the same conditions. The supernatant fluid is decanted, and the remaining sediment is discarded after a sufficient quantity has been accumulated.

The duration, speed, and other particulars of the centrifugation steps described above are not critical. In this example, these were chosen to apply the maximum G-forces to the homogenate and sediment in the most convenient manner, using the equipment available.

As each batch of supernatant fluid is decanted, it is filtered through sterile gauze and then frozen at or below −85° C. for storage. The filtration is not required, but is preferred, because the extract is, in the preferred embodiment, subjected to ultrafiltration. Frozen storage is not essential but is preferred, because it is convenient for subsequent batch-processing.

C. Detoxification

If the filtered extract was frozen, it is thawed, as by a 37° C. water bath. The thawed or non-frozen extract is then detoxified. This treatment is not, per se, necessary to practice the invention, but it is preferred because endotoxins are present in the filtered extract and could injure a patient to whom the pharmaceutical is administered.

In the preferred embodiment, the filtered extract is detoxified.

D. Dilution to Uniform Potency

In the preferred embodiment, the detoxified fluid is then diluted to a uniform potency. This is not, per se, necessary to practice the invention; it is preferred because this facilitates clinical administration.

A cell culture assay is preferably used to assess the potency of the detoxified fluid. This technique measures the effect of various concentrations of the detoxified fluid on the viability of known cancer cell lines. Advantageously, dilutions of 1:10, 1:100 and 1:1000 are applied to the human adenocarcinoma cell line COLO 320DM; a cell density of 3,000 cells per well is used in the assay. The colorimetric agent is MTT, manufactured by Chemicon International, Inc. in El Segundo, Calif. As long as the dose response curve is within the region indicated in FIG. 2, the potency is appropriate. If necessary, dilution is used to achieve an acceptable potency. Advantageously, 0.9% saline solution is used for the dilution, but 5% dextrose solution or intravenous grade water may be used instead.

The diluted fluid is then frozen for storage below $-85°$ C. As before, frozen storage is not part of the invention; it facilitates batch processing.

E. Final Processing

If frozen, the diluted fluid is thawed, as by a 37° C. water bath. The thawed or not-frozen diluted fluid is then sterile filtered by ultrafiltration through a 0.22 micron filter. This process step is standard in the pharmaceutical industry, and is not a part of the invention. Advantageously, this 0.22 micron ultrafiltration is carried out immediately before bottling, and potency is again assessed before bottling is carried out.

Advantageously, the liquid is bottled under sterile conditions into 5 ml, Type I serum, light resistant glass serum vials, which are sealed with a West butyl stopper and a lacqured aluminum seal crimp. The liquid is stored above freezing and below 6° C. It is aspirated by the clinician through a hypodermic needle and diluted as required to facilitate administration.

The pharmaceutical need not be stored in liquid form. After sterilization, the diluted liquid may be freeze-dried (lyophilized) to make storage easier. In this case, the lyophilized pharmaceutical is preferably mixed with diluent, to make administration easier.

DOSAGE PROTOCOLS

Persons skilled in the art know that treatment of tumors is highly individualized in accordance with the medical condition of the patient. Therefore, the following material is only a guide to proper administration, with the actual details and implementation of the dosage being within the sound discretion of the clinician.

The preferred method of administration is by intravenous injection. It is alternatively possible to use injection into the tumor to be treated. Advantageously, one injection is carried out each day until (a) the tumor is completely necrotized, or (b) the tumor is made susceptable to extirpation or debulking and is then removed. Thereafter, one daily injection is continued as an adjuvant treatment for seven more days.

The dosage depends upon the size of the tumor(s) to be treated. Where the tumors are small (e.g. 3 cm or less in diameter), the preferred dosage is 0.00972 cc of diluted liquid per kilogram of patient body weight, for 14 to 21 days. Where the tumors are large (e.g. more than 3 cm in diameter), the preferred dosage is 0.00486 cc of diluted liquid per kilogram of patient body weight, for 21 to 30 days.

It is important not to overdose the patient. This is because tumor necrosis can proceed so rapidly that the body is unable to reabsorb the necrotic tumor tissue. This in itself can be a health risk.

Therefore, it is advantageous to monitor the patient's body functions during therapy. Advantageously, the patient's blood urea nitrogen (BUN), uric acid, total urea, and creatinine are measured prior to the onset of therapy. During administration of the pharmaceutical, these body functions are monitored, and if one or more of them differs significantly from the patient's baseline values, this indicates an excessive rate of tumor necrosis and a discontinuance of therapy until the rate of tumor necrosis is reduced to an acceptable value.

Although a preferred embodiment has been described above, the scope of the invention is limited only by the following claims:

We claim:

1. A pharmaceutical for treating tumors, comprising a biologically active extract derived from fertilized eggs of a frog species.

2. The pharmaceutical of claim 1, wherein the frog is *Rana pipiens*.

3. The pharmaceutical of claim 1, wherein the fertilized eggs are at a stage of development which is prior to gastrulation.

4. The pharmaceutical of claim 3, wherein the fertilized eggs have reached the stage of cleavage.

5. The pharmaceutical of claim 4, wherein the fertilized eggs have reached the 2 to 128 cell stage.

6. The pharmaceutical of claim 1, wherein the extract is detoxified.

7. The pharmaceutical of claim 1, wherein the extract is diluted to a standard therapeutic potency.

8. A pharmaceutical for treating tumors, comprising a biologically active extract derived from homogenized and centrifuged embryos of the *Rana pipiens* frog which have reached the 2 to 128 cell stage of development prior to homogenization and centrifugation and which has been detoxified, and diluted to a standard therapeutic potency.

9. A method of manufacturing a pharmaceutical for treating tumors, comprising the following steps:
   (a) creating embryos of the *Rana pipiens* frog;
   (b) terminating development of the embryos prior to gastrulation;
   (c) mechanically processing the embryos to derive an extract therefrom;
   (d) detoxifying the extract; and
   (e) diluting the detoxified extract to a standard therapeutic potency.

10. The method of claim 9, wherein said creating step comprises the step of inducing ovulation in a *Rana pipiens* female to produce unfertilized eggs.

11. The method of claim 10, wherein said inducing step comprises the step of transplanting at least one pituitary gland from a *Rana pipiens* frog to said female.

12. The method of claim 9, wherein said creating step comprises the step of adding *Rana pipiens* sperm to unfertilized *Rana pipiens* eggs outside the body of a female *Rana pipiens*.

13. The method of claim 12, wherein said sperm is in the form of a solution which includes macerated *Rana pipiens* testes.

14. The method of claim 9, wherein said terminating step is carried out when said embryos are at the 2 to 128 cell stage of cleavage.

15. The method of claim 9, wherein said processing step comprises the step of homogenization.

16. The method of claim 15, wherein said processing step further comprises the step of centrifugation.

17. The method of claim 9, wherein said diluting step further comprises the step of assessing potency by carrying out a cell culture assay.

* * * * *

UNITED STATES PATENT AND TRADEMARK OFFICE
CERTIFICATE OF CORRECTION

PATENT NO. : 4,888,172

DATED : December 19, 1989

INVENTOR(S) : Emil Szebenyi and Kuslima Shogen

It is certified that error appears in the above-identified patent and that said Letters Patent is hereby corrected as shown below:

Title Page, Field [75], change "Shogen Kuslima" to --Kuslima Shogen--

Title Page, Field [73], change "Alfaceu" to --Alfacell--

Signed and Sealed this

Fourth Day of June, 1991

Attest:

HARRY F. MANBECK, JR.

*Attesting Officer*   *Commissioner of Patents and Trademarks*